(12) United States Patent
Gomori

(10) Patent No.: US 11,872,415 B2
(45) Date of Patent: Jan. 16, 2024

(54) DEVICE SYSTEM AND METHOD FOR TRANS-CRANIAL FOCUSED ULTRASOUND WITHOUT HAIR SHAVING

(71) Applicant: John Moshe Gomori, Jerusalem (IL)

(72) Inventor: John Moshe Gomori, Jerusalem (IL)

( * ) Notice: Subject to any disclaimer, the term of this patent is extended or adjusted under 35 U.S.C. 154(b) by 1057 days.

(21) Appl. No.: 16/626,399

(22) PCT Filed: Jul. 3, 2018

(86) PCT No.: PCT/IL2018/050721
§ 371 (c)(1),
(2) Date: Dec. 24, 2019

(87) PCT Pub. No.: WO2019/008579
PCT Pub. Date: Jan. 10, 2019

(65) Prior Publication Data
US 2020/0139161 A1   May 7, 2020

Related U.S. Application Data

(60) Provisional application No. 62/529,189, filed on Jul. 6, 2017.

(51) Int. Cl.
*A61N 7/02* (2006.01)
*A61M 35/00* (2006.01)
*A61N 7/00* (2006.01)

(52) U.S. Cl.
CPC ............... *A61N 7/02* (2013.01); *A61M 35/10* (2019.05); *A61M 35/30* (2019.05); *A61M 2202/0225* (2013.01); *A61M 2205/058* (2013.01); *A61M 2209/088* (2013.01); *A61M 2210/06* (2013.01); *A61N 2007/0039* (2013.01)

(58) Field of Classification Search
CPC .... A61N 7/02; A61N 2007/0039; A61N 7/00; A61M 35/10; A61M 35/30; A61M 2202/0225; A61M 2205/058; A61M 2209/088; A61M 2210/06; A61B 17/2251
See application file for complete search history.

(56) References Cited

U.S. PATENT DOCUMENTS

| | | | |
|---|---|---|---|
| 2005/0171457 A1* | 8/2005 | Yang | A61H 7/001 601/17 |
| 2008/0276954 A1 | 11/2008 | Pienaar | |
| 2012/0289869 A1 | 11/2012 | Tyler | |

(Continued)

OTHER PUBLICATIONS

Eames et al (2013) Trans-cranial focused ultrasound without hair shaving: feasibility study in an ex vivo cadaver model, Journal of Therapeutic Ultrasound, 1:24.

(Continued)

*Primary Examiner* — Hien N Nguyen
(74) *Attorney, Agent, or Firm* — The Roy Gross Law Firm, LLC; Roy Gross

(57) ABSTRACT

Device for shave-free trans-cranial focused ultrasound (FUS) treatment and method for using same, the device including a scalp cover having a first inlet configured to allow supply of a gas into the scalp cover, and an outlet configured to allow outflow of ambient air contained within the scalp cover when the gas is being supplied, such that the ambient air contained within the scalp cover is replaced by the supplied gas.

17 Claims, 4 Drawing Sheets

(56) References Cited

U.S. PATENT DOCUMENTS

| | | | |
|---|---|---|---|
| 2018/0021021 A1* | 1/2018 | Zwierstra | A61N 7/00 |
| | | | 600/453 |
| 2018/0177491 A1* | 6/2018 | Hynynen | A61B 34/10 |
| 2019/0021666 A1* | 1/2019 | Hynynen | A61B 90/14 |

OTHER PUBLICATIONS

Khanna et al (2017) Intracranial Applications of MR Imaging-Guided Focused Ultrasound, American Society of Neuroradiology.
International Search Report and Written Opinion, International Application No. PCT/IL2018/050721, dated Oct. 9, 2018.

* cited by examiner

DEVICE SYSTEM AND METHOD FOR TRANS-CRANIAL FOCUSED ULTRASOUND WITHOUT HAIR SHAVING

RELATED APPLICATIONS

This application is a National Phase of PCT Patent Application No. PCT/IL2018/050721 having International filing date of Jul. 3, 2018, which claims the benefit of priority of U.S. Provisional Application No. 62/529,189 filed on Jul. 6, 2017 entitled DEVICE, SYSTEM AND METHOD FOR TRANS-CRANIAL FOCUSED ULTRASOUND WITHOUT HAIR SHAVING. The contents of the above applications are all incorporated by reference as if fully set forth herein in their entirety.

TECHNICAL FIELD

The disclosure generally relates to devices, systems and methods for noninvasive transcranial thermal treatment, specifically high-intensity focused ultrasound (HIFU), which does not require prior shaving of the subject's hair.

BACKGROUND

Focused ultrasound (FUS), or high-intensity focused ultrasound (HIFU), involves depositing ultrasonic energy into a target volume, where the area of acoustic emission is significantly greater than the focal area. This focusing effect allows generation of a high level of acoustic intensity at the target volume, thereby causing a variety of thermal to mechanical bio-effects. Currently, the most common usage of FUS in clinical practice is for noninvasive thermal ablation with close to 100,000 patients treated worldwide, including prostate cancer, liver cancer, breast cancer, and symptomatic uterine fibroids.

Being a noninvasive, accurate, radiation-free thermal ablation tool, FUS has long been viewed as an ideal treatment tool for various brain indications, such as, but not limited to, brain cancers, tremor and neurological diseases. In addition, its clinical potential is emerging as it offers a unique opportunity to deliver drugs to a localized brain area for patients with neurological disorders by opening the blood brain barrier (BBB), an approach that can enhance the therapeutic effect and decrease whole-brain influence. However, since the efficiency of FUS may be negatively impacted by air bubbles trapped in the patient's hair, which air bubbles are known to not only block ultrasound but also absorb ultrasonic energy, current practice involves shaving the patient's head on treatment day. This practice, although noninvasive and scientifically and clinically sound, is often a concern to patients, especially when repeated treatments are needed. In addition, shaving of the patient presents a potential limitation if and when there is a need for a repeated trans-cranial MRI guided FUS (tcMRgFUS) in the cases of a BBB opening that needs to be synced with chemotherapy administration or when 'time to treat' is limited, as could be the case in stroke clot lysis.

There is thus an unmet need for a device and method allowing efficient and accurate trans-cranial FUS, while obviating the need for hair shaving.

SUMMARY OF THE INVENTION

The present disclosure relates to devices, systems and methods for providing noninvasive trans-cranial thermal ablation, such as trans-cranial focused ultrasound (FUS) treatment, especially high-intensity focused ultrasound (HIFU), FUS-induced BBB opening and/or FUS-mediated neuromodulation, without the need for hair shaving.

The herein disclosed device and method include a scalp cover configured to be worn by the subject prior to the transcranial ultrasound treatment. The scalp cover is configured to facilitate supply of a gas into the cover in such manner that the supplied gas replaces/expels/substitutes ambient air trapped on and/or between the subject's hair. Due to its high solubility in water, the supplied gas efficiently dissolves in the water, such that the subject's hair becomes essentially free of air bubbles. As a result, an effective, essentially undisturbed FUS treatment can be provided without the need for the subject to have his/her hair shaved off prior to the treatment.

Selective disruption of the BBB by focus ultrasound, followed by administration of anti-cancer agents, represents a promising approach for treatment of neurological disease, such as but not limited to, glioma. However, due to the fact that the shaving of the patient's head is needed each time the drug needs to be administered, the need for head shaving may become a limitation and even an obstacle to the drug administration. Obviating the need for shaving of the patient's head is thus an important advantage.

Advantageously, the supplied gas may be carbon dioxide ($CO_2$), which does not pose a health hazard to the subject.

In addition, the scalp cover may be easy to wear, low cost, disposable, and formed of a material essentially transparent to the FUS treatment as well as to magnetic resonance (MRI) (MRgFUS) or ultrasound imaging accompanying/guiding the treatment.

According to some embodiments, there is provided a method for shave-free trans-cranial focused ultrasound (FUS) treatment, the method comprising placing a scalp cover on a head of a subject in need of trans-cranial FUS, such that said scalp cover essentially seals around the subject's scalp, supplying a gas into the scalp cover such that ambient air covering the patient's scalp is replaced by the supplied gas; wherein the gas has a higher solubility in water than the ambient air, sending a flow of an aqueous fluid into the scalp cover such that the subject's hair is submerged and/or wet, and providing a trans-cranial focused ultrasound (FUS) treatment to the subject.

According to some embodiments, the trans-cranial focused ultrasound (FUS) treatment may be high-intensity focused ultrasound (HIFU). According to some embodiments, the HIFU may be pulsed or continuous. According to some embodiments, the trans-cranial focused ultrasound (FUS) treatment comprises low-intensity focused ultrasound (LIFU). According to some embodiments, the LIFU may be pulsed or continuous.

According to some embodiments, the trans-cranial focused ultrasound (FUS) treatment may be or include a FUS-induced BBB opening, for example achieved by providing pulsed HIFU. According to some embodiments, the FUS-induced BBB opening treatment may include administering a contrast agent prior to the treatment. According to some embodiments, the FUS-induced BBB opening treatment may include administering a drug during or after the treatment.

According to some embodiments, the trans-cranial focused ultrasound (FUS) treatment may be or include FUS-mediated neuromodulation, for example achieved by providing pulsed LIFU.

According to some embodiments, the trans-cranial focused ultrasound (FUS) treatment may be for ablation of a tissue (e.g. a tumor), for example achieved by providing continuous HIFU.

According to some embodiments, the gas has a solubility in water above 1 g/L at 25° C. at 100 kPA. According to some embodiments, the gas is $CO_2$.

According to some embodiments, the aqueous fluid is degassed water. According to some embodiments, the aqueous fluid is a hydrogel.

According to some embodiments, the subject's hair is essentially free of air bubbles prior to the initiation of the treatment.

According to some embodiments, providing the trans-cranial FUS treatment to the subject includes placing a helmet-like head wearable, housing a FUS transducer, on top of the scalp cover.

According to some embodiments, the scalp cover is made of a material essentially transparent to the FUS.

According to some embodiments, the supplying of the gas into the scalp cover, may include sending the flow of the gas through an inlet formed in the scalp cover.

According to some embodiments, the flowing of the aqueous fluid into the scalp cover may include sending the flow of the aqueous fluid through the same or a different outlet formed in the scalp cover.

According to some embodiments, replacing the ambient fluid may include allowing ambient air to exit the scalp cover through an outlet formed therein.

According to some embodiments, the FUS treatment is provided without prior shaving of the subject's hair.

According to some embodiments, there is provided a device for shave-free trans-cranial focused ultrasound (FUS) treatment, the device including a scalp cover, the scalp cover including a first inlet configured to allow supply of a gas into the scalp cover, and an outlet configured to allow outflow of ambient air contained within the scalp cover when the gas is being supplied, such that the ambient air contained within the scalp cover is replaced by the supplied gas.

According to some embodiments, the scalp cover is sized and shaped to essentially seal the scalp cover around a subject's scalp, when worn.

According to some embodiments, the scalp cover further includes a second inlet configured to allow supply of an aqueous fluid into the scalp cover. According to some embodiments, the first inlet is further configured to allow supply of the aqueous fluid into the scalp cover.

According to some embodiments, the gas has a solubility in water above 1 g/L at 25° C. at 100 kPA. According to some embodiments, the gas is $CO_2$.

According to some embodiments, the scalp cover is a cap.

According to some embodiments, the trans-cranial FUS treatment is trans-cranial high-intensity focused ultrasound (HIFU).

According to some embodiments, the trans-cranial FUS treatment is a FUS-treatment configured to induce BBB opening treatment. According to some embodiments, the FUS-treatment configured to induce BBB opening treatment may be pulsed HIFU.

According to some embodiments, the trans-cranial FUS treatment is a FUS-treatment configured to induce neuromodulation. According to some embodiments, the FUS-treatment configured to induce neuromodulation may be pulsed LIFU.

According to some embodiments, the trans-cranial FUS treatment is a FUS-treatment configured to ablate tissue (e.g. solid tumors). According to some embodiments, the FUS-treatment configured to ablate treatment may be continuous HIFU.

According to some embodiments, the scalp cover is made from a material configured to allow essentially undisturbed passage of the FUS therethrough.

According to some embodiments, the first and/or the second inlet may include a valve. According to some embodiments, the valve may be a one-way valve configured to prevent backflow of the supplied gas and/or the aqueous fluid.

According to some embodiments, the first inlet is positioned on an opposite side of the scalp cover than the outlet.

According to some embodiments, the scalp cover may further include a sensor configured to determine the concentration of the gas within the scalp cover.

According to some embodiments, the aqueous fluid is configured to be supplied when a concentration of the supplied gas within the scalp cover reaches a predetermined threshold. According to some embodiments, the aqueous fluid is configured to be supplied a predetermined time after the gas is being supplied.

According to some embodiments, the outlet is configured to be closed when the ambient air has been replaced by the supplied gas.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION OF THE INVENTION

Figure 1:
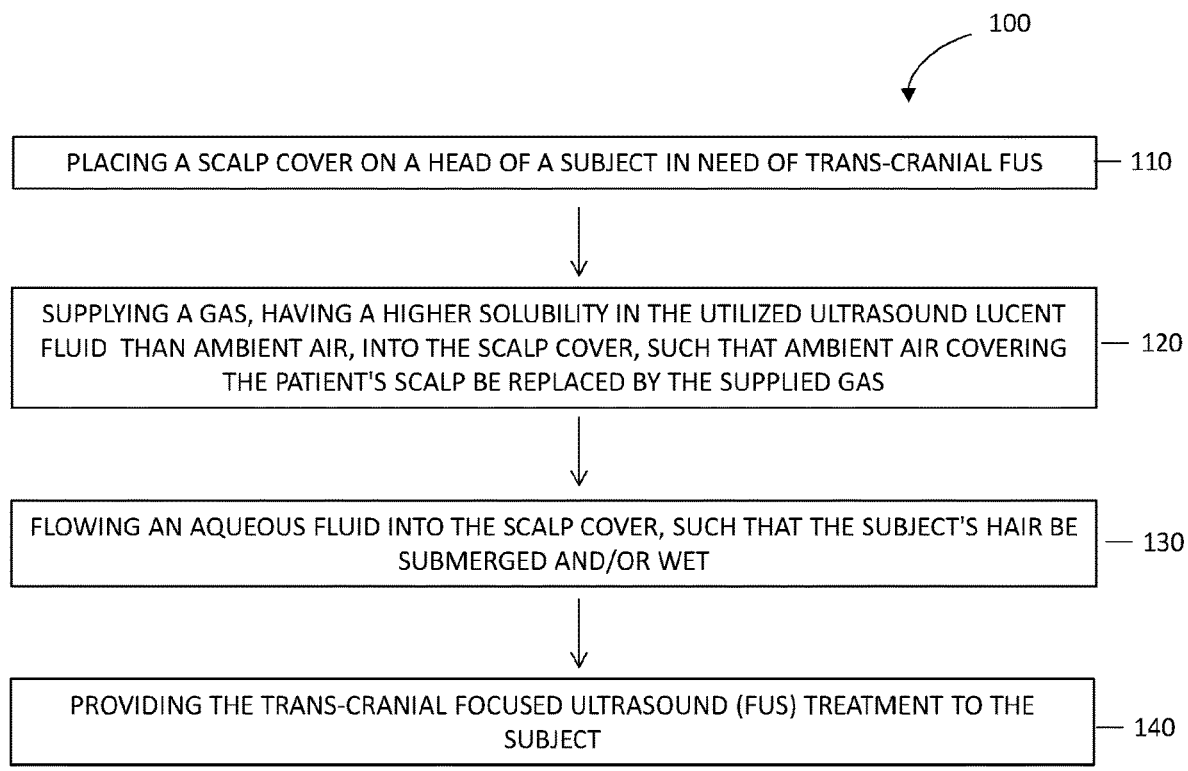
FIG. 1 is an illustrative flow chart of a method for shave-free trans-cranial focused ultrasound (FUS) treatment, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a device for shave-free trans-cranial focused ultrasound (FUS) treatment, the device comprising a scalp cover, including a first inlet configured to allow supply of a gas into the scalp cover (between the subject's scalp and the cover), and an outlet configured to allow outflow of ambient air contained within the scalp cover, when the gas is being supplied, such that the ambient air contained within the scalp cover is replaced by the supplied gas. According to some embodiments, the inlet may be directly or indirectly connected (for example through a tube) to a gas supply.

As used herein, the term "shave-free trans-cranial focused ultrasound (FUS) treatment" refers to a FUS treatment provided to the subject's brain, which does not require the subject's head to be shaved prior thereto.

According to some embodiments, focused ultrasound (FUS) treatment may be therapeutic FUS relying on acoustic wave propagation directed at a specific focus, generating high-resolution focal energy deposition while sparing intervening and adjacent tissues.

According to some embodiments, the focused ultrasound (FUS) treatment may be trans-cranial high-intensity focused ultrasound (HIFU). According to some embodiments, the HIFU may be pulsed HIFU. According to some embodiments, the HIFU may be continuous HIFU. According to some embodiments, the focused ultrasound (FUS) treatment may be trans-cranial low-intensity focused ultrasound (LIFU). According to some embodiments, the LIFU may be pulsed LIFU. According to some embodiments, the LIFU may be continuous LIFU.

According to some embodiments, the focused ultrasound (FUS) treatment may be a FUS-induced BBB opening. According to some embodiments, the FUS-induced BBB opening may be a non-ablative FUS-induced BBB. According to some embodiments, the focused ultrasound (FUS) treatment may be a FUS-mediated neuromodulation, i.e. ultrasound mediated alteration of nerve activity. According to some embodiments, the FUS-mediated neuromodulation may be a non-ablative FUS-mediated neuromodulation.

According to some embodiments, the trans-cranial FUS treatment may refer to a treatment configured to generate a localized effect, such as heating, boiling, or cavitation of tissue, leading to its ablation. According to some embodiments, the FUS treatment may be for treatment of a focal point in the Vim nucleus of the thalamus, responsible for causing tremors. According to some embodiments, the FUS treatment may be for treatment of tremor, epilepsy, brain cancer, stroke clot lysis, Parkinson, Alzheimer, dementia, depression, obsessive-compulsive disorder (OCD), or other neurological disease. Each possibility is a separate embodiment. According to some embodiments, the HIFU treatment may be used as a non-invasive brain surgery tool.

According to some embodiments, the FUS energy may generate heat at a focal point of up to 65-85° C., 70-90° C., or 75-90° C., such as for example 85° C., and optionally to ablate targeted tissue. According to some embodiments, the frequencies used for the therapeutic ultrasound are in the range of 150 KHz-800 KHz, 200 KHz-700 KHz or 220 KHz to 680 KHz. Each possibility is a separate embodiment.

According to some embodiments, during treatment, 500-1500 or 750-1250 rays (e.g. 1000 rays) of ultrasound are emitted to a focal point. Each possibility is a separate embodiment.

According to some embodiments, the ultrasound treatment may be guided by MRI (MRgFUS), thereby providing a clear vision of the treated tissue.

According to some embodiments, the focused ultrasound (FUS) treatment may be a trans-cranial FUS-induced BBB opening. According to some embodiments, the FUS-induced BBB opening may be a non-ablative FUS-induced BBB opening. The blood-brain barrier (BBB) poses a significant impediment for the delivery of therapeutic drugs into the brain. This is particularly problematic for example in the treatment of malignant gliomas which are characterized by diffuse infiltration of tumor cells into a normal brain, where they are protected by a potent BBB. Selective disruption of the BBB by focus ultrasound, followed by administration of anti-cancer agents, thus represents a promising approach for the elimination of infiltrating glioma cells. However, due to the fact that the shaving of the patient's head is needed each time the drug needs be administered, the need for head shaving may become a limitation and even an obstacle to drug administration.

According to some embodiments, the focused ultrasound (FUS) treatment may be provided concomitant with an ultrasound contrast agent serving to ensure BBB opening without concomitant damage to normal brain tissue. Typically, the contrast agent is injected intravenously a few seconds prior to the FUS treatment. According to some embodiments, the contrast agents (e.g. Optison®) may include albumin coated microbubbles. Without being bound by any theory, the microbubbles circulating in the vasculature confine the ultrasound effects to the blood vessel walls, resulting in BBB disruption with minimal damage to surrounding brain tissue. According to some embodiments, the introduction of contrast agents may allow selective disruption of the BBB at much lower acoustic power levels than previously employed, making this approach substantially easier to apply through the intact skull which is highly absorbing of ultrasound.

According to some embodiments, the focused ultrasound (FUS) treatment may be trans-cranial FUS-induced neuromodulation. According to some embodiments, the trans-cranial FUS-induced neuromodulation may be non-ablative trans-cranial FUS-induced neuromodulation.

According to some embodiments, the thermal data may be analyzed, optionally in real-time, to determine the cumulative thermal impact on the tissue. According to some embodiments, the treatment may include adjusting treatment parameters so as to ensure a safe and effective response.

According to some embodiments, the gas supplied to the scalp cover, prior to the ultrasound treatment, is a gas having a solubility in water above 0.5 g/L, above 0.75 g/L or above 1 g/L at 25° C. at 100 kPA. According to some embodiments, the gas may have a solubility in water of 1.45 g/L at 25° C. at 100 kPA. According to some embodiments, the gas supplied to the scalp cover, prior to the ultrasound treatment, may be $CO_2$.

As used herein, the term "scalp cover" may refer to any head wear configured to be worn by the subject so as to cover the part of the subject's head covered by hair. According to some embodiments, the scalp cover may be a hat, a helmet, a cap, a scarf or any other suitable head cover. According to some embodiments, the scalp cover may be essentially similar in shape to a swim cap or a shower cap. According to some embodiments, the scalp cover is made from a material configured to allow essentially undisturbed passage of the HIFU therethrough. Non-limiting examples of suitable materials include plastic, rubber, silicone rubber substitutes and/or combinations thereof.

According to some embodiments, the scalp cover may be sized and shaped to essentially seal the scalp cover around a subject's scalp, when worn. As used herein, the term "seal", may refer to a cover, which once worn, does not allow substantial entrance of ambient air into the cover. As used herein, the term "essentially" with regards to the sealing may refer to a head cover closing around the subject's scalp in such manner that amounts of air capable of interfering with the ultrasound treatment are prevented from entering the head cover. As a non-limiting example, the scalp cover may include a rubber band or other element configured to close the scalp cover around the subject's scalp.

According to some embodiments, the scalp cover may include internal sprinkler channels, connected to the inlet, the sprinkler channels configured to allow efficient spreading/dispersion/distribution of the supplied gas around the subject's scalp and/or hair. As used herein, the term "sprinkler channel" may refer to interconnected tubes having outlets or pores through which the gas, and optionally the aqueous fluid, can be dispersed.

According to some embodiments, the first inlet is further configured to allow supply of an aqueous fluid into the scalp cover, for example through a direct or indirect connection to a container, or other reservoir, containing the fluid. According to some embodiments, the tube interconnecting the inlet to the gas supply and the water reservoir may include a switch valve configured to switch the supply from the gas reservoir to the reservoir of the aqueous fluid, when required.

Additionally or alternatively, the scalp cover may include a second inlet configured to allow supply of the aqueous fluid into the scalp cover, for example through a direct or indirect connection (e.g. through a tube) to a reservoir containing the fluid. According to some embodiments, the second inlet may be connected to the same or a different set of sprinkler channels, configured to allow efficient spreading/dispersion/distribution of the aqueous fluid around the subject's scalp and/or hair. As used herein, the term "sprinkler channel" may refer to interconnected tubes having outlets or pores through which the gas, and optionally the aqueous fluid, can be dispersed.

According to some embodiments, the first and/or second inlets may include a valve. According to some embodiments, the valve may be a one-way valve configured to prevent backflow of the supplied gas and/or the aqueous fluid. This may be of particular importance if the gas and/or the fluid is not provided during the entire treatment.

According to some embodiments, the first inlet may be positioned on an opposite side of the scalp cover than the outlet or at any other suitable distance from the outlet to ensure that the supplied gas does not escape the outlet prior to reaching the subject's hair and/or prior to ambient air, trapped on the subject's hair, has been replaced with the supplied gas.

According to some embodiments, the scalp cover may further include a sensor configured to determine the concentration of the supplied gas within the scalp cover. According to some embodiments, the sensor may be configured to provide a signal indicative of the supplied gas having reached a predetermined concentration and/or indicative of ambient air, trapped in the subject's hair, having been replaced with the supplied gas. According to some embodiments, once the signal has been obtained from the sensor, the supply of the gas may, optionally automatically, be stopped and/or the first inlet be closed. According to some embodiments, once the signal has been obtained from the sensor, the supply of the aqueous fluid may (optionally automatically) be commenced, through the same (first) or the second inlet. According to some embodiments, once the signal has been obtained from the sensor, the outlet, through which the ambient air is expelled, may (optionally automatically) be closed so as to prevent (additional) escape of the supplied gas therethrough.

According to some additional or alternative embodiments, the supply of the gas may, optionally automatically, be stopped and/or the first inlet be closed a predetermined time period after the supply of the gas is commenced. Similarly, according to some additional or alternative embodiments, the supply of the aqueous fluid may (optionally automatically) be commenced, through the same (first) or the second inlet, at a predetermined time period after the supply of the gas is commenced. Similarly, according to some additional or alternative embodiments, the outlet, through which the ambient air is expelled, may (optionally automatically) be closed at a predetermined time period after the supply of the gas is commenced, so as to prevent (additional) escape of the supplied gas therethrough. According to some embodiments, the scalp cover may include a timer configured to time the onset of the supply of the aqueous fluid and/or the closing of the inlet(s) and/or outlet.

According to some embodiments, there is provided a method for shave-free focused ultrasound (FUS) treatment, the method including supplying a gas to a subject such that ambient air covering the subject's hair will be replaced by the supplied gas, wetting and/or submerging the subject's hair in an aqueous fluid, and providing a focused ultrasound (FUS) treatment to the subject. According to some embodiments, the FUS treatment is provided without prior shaving of the subject's hair.

According to some embodiments, the FUS treatment is trans-cranial FUS. However according to some embodiments, the method is likewise suitable for treatment of other areas of the subject's body covered by hair.

According to some embodiments, the method may include placing a scalp cover on ahead of a subject in need of trans-cranial FUS treatment, prior to the FUS treatment, such that the scalp cover essentially seals around the subject's scalp. According to some embodiments, the scalp cover may be the scalp cover disclosed herein. According to some embodiments, the supplying of the gas may include, flowing the gas into the head cover.

According to some embodiments, the focused ultrasound (FUS) treatment may be high-intensity focused ultrasound (HIFU). According to some embodiments, the focused ultrasound (FUS) treatment may be a trans-cranial FUS-induced BBB opening. As explained herein, the blood-brain barrier (BBB) poses a significant impediment for the delivery of therapeutic drugs into the brain. Trans-cranial FUS-induced BBB opening, thus represents a promising approach. However, due to the fact that the shaving of the patient's head is needed each time the drug needs be administered, the need for head shaving may become a limitation and even an obstacle to drug administration.

According to some embodiments, the focused ultrasound (FUS) treatment may be trans-cranial FUS-induced neuromodulation. According to some embodiments, the trans-cranial FUS-induced neuromodulation may be non-ablative.

According to some embodiments, the method may further include providing an ultrasound contrast agent, prior to the treatment. Typically, the contrast agent is injected intravenously a few seconds prior to the FUS treatment. According to some embodiments, the contrast agent may serve to ensure a BBB opening without concomitant damage to normal brain tissue. According to some embodiments, the contrast agents (e.g. Optison®) may include albumin coated microbubbles. As explained herein, the microbubbles may confine the ultrasound effects to the blood vessel walls, resulting in BBB disruption with minimal damage to surrounding brain tissue. According to some embodiments, the introduction of contrast agents may allow selective disruption of the BBB at lower acoustic power levels than previously employed, making this approach substantially easier to apply through the intact skull which is highly absorbing of ultrasound.

According to some embodiments, the subject's hair is essentially free of air bubbles prior to the initiation of the treatment, as a result of the providing of the gas. According to some embodiments, the ultrasound rays of the FUS treatment may be essentially undisturbed. As a result, the efficiency, as well as the reproducibility of the treatment, may be significantly increased, optionally despite inter-subject hair-differences. It is understood that reducing the ultrasound absorption by air-bubbles trapped in the subject's hair may require much less computational power yet ensure high accuracy, in that adjustments of treatment parameters due to the absorption may not be required.

According to some embodiments, the amount of gas supplied may be adjusted based on inter-subject differences such as hair length, hair density and the like. This may on the one hand ensure that all trapped air be efficiently replaced by the supplied gas yet reduce unnecessary waste.

According to some embodiments, the gas supplied has a higher solubility in water than the ambient air. According to some embodiments, the gas has a solubility in water above 0.7 g/L, above 0.8 g/L or above 1 g/L at 25° C. at 100 kPA. Each possibility is a separate embodiment.

According to some embodiments, the gas supplied has a higher solubility in the ultrasound lucent fluid utilized for the treatment than ambient air.

According to some embodiments, the gas is $CO_2$.

According to some embodiments, the FUS energy may generate heat at a focal point of up to 65-85° C., 70-90° C., or 75-90° C., such as for example 85° C., to ablate targeted tissue.

According to some embodiments, the frequencies used for therapeutic ultrasound are in the range of 150 KHz-800 KHz, 200 KHz-700 KHz or 220 KHz to 680 KHz. Each possibility is a separate embodiment.

According to some embodiments, the aqueous fluid may be degassed water. According to some embodiments, aqueous fluid may be a hydrogel. According to some embodiments, the aqueous fluid may be any ultrasound lucent fluid that is not toxic or irritating to scalp and hair. According to some embodiments, the aqueous liquid may be cooled prior to treatment, such as but not limited to, cooled degassed water. According to some embodiments, the aqueous fluid is sent flowing into the scalp cover, as essentially described herein. According to some embodiments, the supplying of the gas into the scalp cover, includes sending a flow of the gas through an inlet formed in the scalp cover, as essentially described herein. According to some embodiments, the flowing of the aqueous fluid into the scalp cover comprises sending the flow of the aqueous fluid through the same outlet as the supplied gas. Additionally or alternatively, the aqueous fluid may be supplied through a different inlet formed in the scalp cover.

According to some embodiments, the replacing of the ambient air includes allowing ambient air to exit the scalp cover through an outlet formed therein, as essentially described herein.

According to some embodiments, the providing of the trans-cranial FUS treatment to the subject includes placing a helmet-like head wearable, housing a FUS transducer, on top of the scalp cover. According to some embodiments, the transducer may be a single-element transducers or a multi-element phased array transducer, optionally allowing electronic steering of the focal zone. According to some embodiments, the trans-cranial FUS treatment is provided by an MR imaging-guided FUS (MRgFUS) apparatus configured to individually steer up to 1024 ultrasound elements to compensate for predicted acoustic wave distortions at the soft-tissue-calvarial interface. Focused transcranial acoustic wave propagation can then be achieved with a resolution of approximately 1 mm.

According to some embodiments, the method may further include obtaining measurements from a sensor indicative of the concentration of the supplied gas and/or ambient air within the scalp cover, and/or indicative of the supplied gas having reached a predetermined concentration and/or indicative of ambient air, trapped in the subject's hair, having been replaced by the supplied gas. According to some embodiments, the method may further include stopping/ceasing/terminating the supply of the gas, based on the signal obtained from the sensor. According to some embodiments, the method may further include closing the gas supply inlet, when a signal has been obtained from the sensor, which is indicative of the supply having reached a predetermined value and/or which indicates that the ambient air has essentially entirely been replaced by the supplied gas.

According to some embodiments, the supply of the aqueous fluid may be commenced, when a signal has been obtained from the sensor which is indicative of the supply having reached a predetermined value and/or which indicates that the ambient air has essentially entirely been replaced by the supplied gas. According to some embodiments, the method may further include closing the outlet through which the ambient air is expelled, when a signal has been obtained from the sensor, which is indicative of the supply having reached a predetermined value and/or which indicates that the ambient air has essentially entirely been replaced by the supplied gas.

According to some additional or alternative embodiments, the supply of the gas may, optionally automatically, be stopped and/or the first inlet be closed a predetermined time period after the supply of the gas is commenced. Similarly, according to some additional or alternative embodiments, the supply of the aqueous fluid may (optionally automatically) be commenced, through the same (first) or the second inlet, at a predetermined time period after the supply of the gas is commenced. Similarly, according to some additional or alternative embodiments, the outlet, through which the ambient air is expelled, may (optionally automatically) be closed at a predetermined time period after the supply of the gas is commenced, so as to prevent (additional) escape of the supplied gas therethrough.

Reference is now made to FIG. 1 which is an illustrative flow chart of a method 100 for shave-free trans-cranial focused ultrasound (FUS) treatment, according to some embodiments. In step 110 of the method a scalp cover, such as the scalp cover disclosed herein, is placed on a head of a subject in need of trans-cranial FUS, such that the scalp cover essentially seals around the subject's scalp. In step 120 of the method, a gas is supplied into the scalp cover, causing the ambient air covering the patient's scalp to be replaced by the supplied gas. The gas is preferably a gas having a higher solubility in the utilized ultrasound lucent fluid (e.g. water) than the ambient air and which does not pose a health hazard to the subject. A non-limiting example of a suitable gas is $CO_2$. In step 130, an aqueous fluid is sent flowing into the scalp cover, such that the subject's hair is submerged and/or wet. The aqueous fluid may be any fluid or semi-fluid suitable for efficient transmittal of the ultrasound rays to a target area in the subject's brain. A non-limiting example of a suitable aqueous fluid is degassed water. In step 140 of the method, trans-cranial focused ultrasound (FUS) treatment, such as, but not limited to, a high intensity focused ultrasound (HIFU) or low intensity focused ultrasound, is provided to the subject, through the scalp cover. According to some embodiments, the trans-cranial FUS treatment may be transcranial MRI guided FUS (tcMRgFUS). Advantageously, due to the discard of ambient air and thus of air bubbles formed on or trapped between the subject's hair, the FUS is delivered essentially undisturbed to the target area in the subject's brain, thus enabling efficient thermal ablation thereof. According to some embodiments, the FUS treatment may be for treatment of a focal point in the Vim nucleus of the thalamus, responsible for causing tremors. According to some embodiments, the FUS treatment may be for treatment of tremor, epilepsy, brain cancer, stroke clot lysis, Parkinson, Alzheimer, dementia, depression, obsessive-compulsive disorder (OCD), or other neurological disease. According to some embodiments, the FUS treatment may be used for non-invasive brain surgery. According to some embodiments, the FUS treatment may be a FUS-induced BBB-opening. According to some embodiments, the FUS-induced BBB-opening may be non-ablative. According to some embodiments, the FUS treatment may be a FUS-induced BBB-opening concomitant with providing of a contrast agent configured to reduce damage to surrounding brain tissue. According to some embodiments, the FUS treatment may be FUS-mediated neuromodulation. According to some embodiments, the FUS-mediated neuromodulation may be non-ablative neuromodulation.

According to some embodiments, the FUS energy may generate heat at a focal point of up to for example 85° C., thus ablating the targeted tissue. According to some embodiments, the FUS is provided at frequencies in the range of 220 KHz to 680 KHz.

Figure 2:
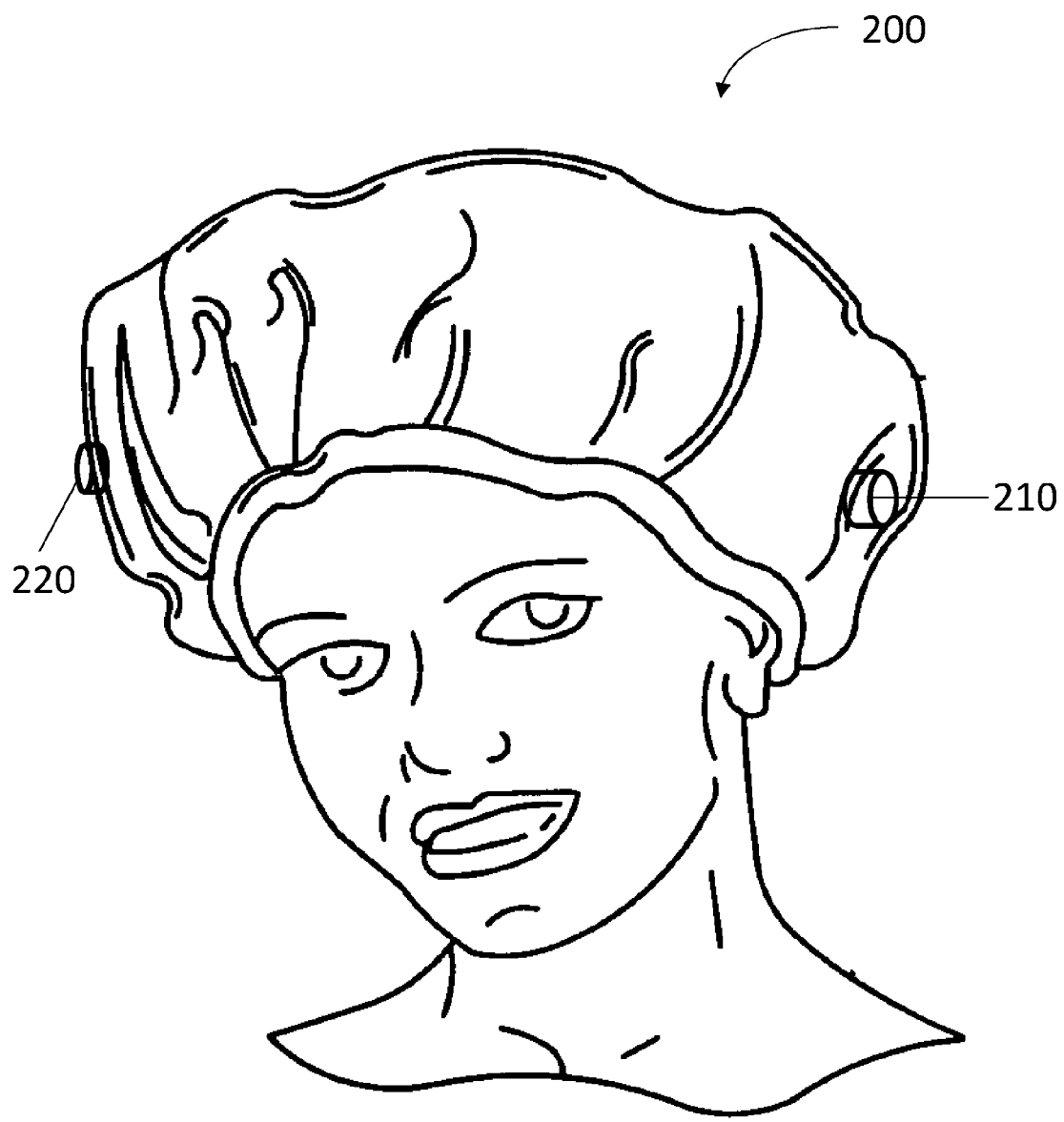
FIG. 2 schematically illustrates a scalp cover for shave-free trans-cranial focused ultrasound (FUS) treatment with a single inlet, according to some embodiments.

Reference is now made to FIG. 2, which schematically illustrates a scalp cover 200 for shave-free trans-cranial focused ultrasound (FUS) treatment, according to some embodiments. Scalp cover 200 includes an inlet 210, configured to allow supply of a gas having a higher solubility in water (or other utilized ultrasound lucent fluid) than ambient air (e.g. $CO_2$), into scalp cover 200, and an outlet 220, configured to allow outflow of ambient air contained within scalp cover 200, when the gas is being supplied, such that the ambient air contained within scalp cover 200 is replaced by the supplied gas. Inlet 210 is, as here shown, optionally positioned on an opposite side of scalp cover 200 than outlet 220, or at any other suitable distance from outlet 220 to ensure that the supplied gas does not immediately escape through outlet 220, prior to reaching the subject's hair and/or prior to ambient air, trapped on the subject's hair, having been efficiently replaced by the supplied gas. Scalp cover 200 is here shown to be in the shape of a shower cap; however, other configurations are also possible and within the scope of this disclosure. According to some embodiments, scalp cover 200 is made from a material configured to allow essentially undisturbed passage of the FUS therethrough, as essentially described herein. Inlet 210 is further configured to allow supply of an aqueous fluid (e.g. degassed water) into scalp cover 200. According to some embodiments, inlet 210 may include a valve (not shown). The valve may optionally be a one-way valve configured to prevent backflow of the supplied gas and/or the aqueous fluid. According to some embodiments, scalp cover 200 may further include a sensor (not shown) configured to determine the concentration of the supplied gas within the scalp cover. According to some embodiments, the sensor may be configured to provide a signal indicative of the supplied gas having reached a predetermined concentration and/or indicative of ambient air, trapped in the subject's hair, having been replaced by the supplied gas, as essentially described herein.

Figure 3:
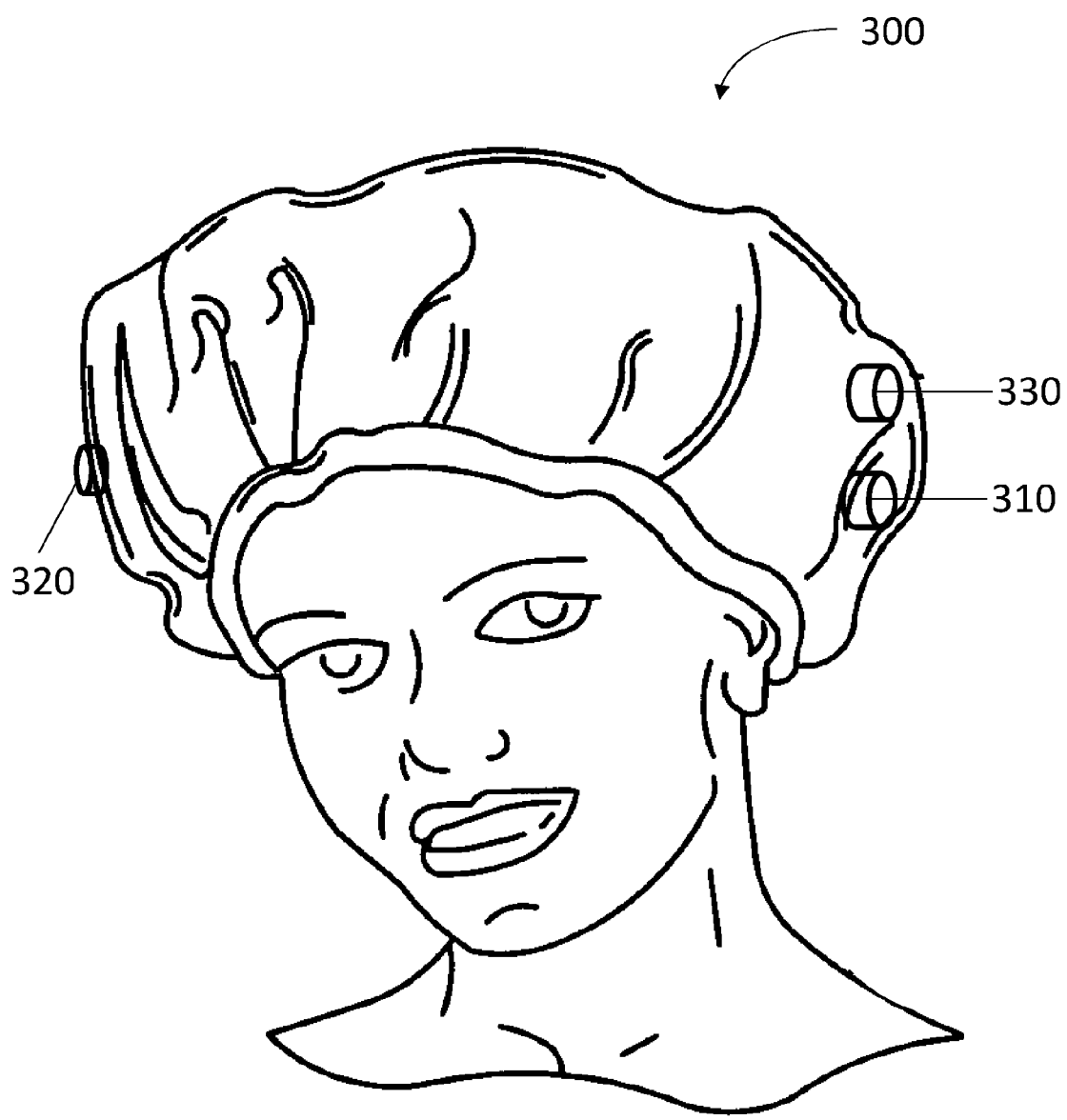
FIG. 3 schematically illustrates a scalp cover for shave-free trans-cranial focused ultrasound (FUS) treatment with two inlets, according to some embodiments.

Reference is now made to FIG. 3, which schematically illustrates a scalp cover 300 for shave-free trans-cranial focused ultrasound (FUS) treatment, according to some embodiments. Scalp cover 300 includes an inlet 310 configured to allow supply of a gas, having a higher solubility in water (or other utilized ultrasound lucent fluid) than ambient air (e.g. $CO_2$), into scalp cover 300, and an outlet 320 configured to allow outflow of ambient air contained within scalp cover 300, when the gas is being supplied, such that the ambient air contained within scalp cover 300 is replaced by the supplied gas. Inlet 310 is, as here shown, optionally positioned on an opposite side of scalp cover 300 than outlet 320 or at any other suitable distance from outlet 320 to ensure that the supplied gas does not immediately escape through outlet 320 prior to reaching the subject's hair and/or prior to ambient air, trapped in the subject's hair, having been replaced by the supplied gas. Scalp cover 300 is here shown to be in the shape of a shower cap; however, other configurations are also possible and within the scope of this disclosure. According to some embodiments, scalp cover 300 is made from a material configured to allow essentially undisturbed passage of the FUS therethrough, as essentially described herein. Scalp cover 300 further includes a second inlet 330 configured to allow supply of an aqueous fluid (e.g. degassed water) into scalp cover 300. According to some embodiments, inlet 310 and/or second inlet 330 may include valves (not shown). The valves may optionally be one-way valves configured to prevent backflow of the supplied gas and/or the aqueous fluid. According to some embodiments, scalp cover 300 may further include a sensor (not shown) configured to determine the concentration of the supplied gas within the scalp cover. According to some embodiments, the sensor may be configured to provide a signal indicative of the supplied gas having reached a predetermined concentration and/or indicative of ambient air, trapped on the subject's hair, has been replaced with the supplied gas, as essentially described herein.

Figure 4:
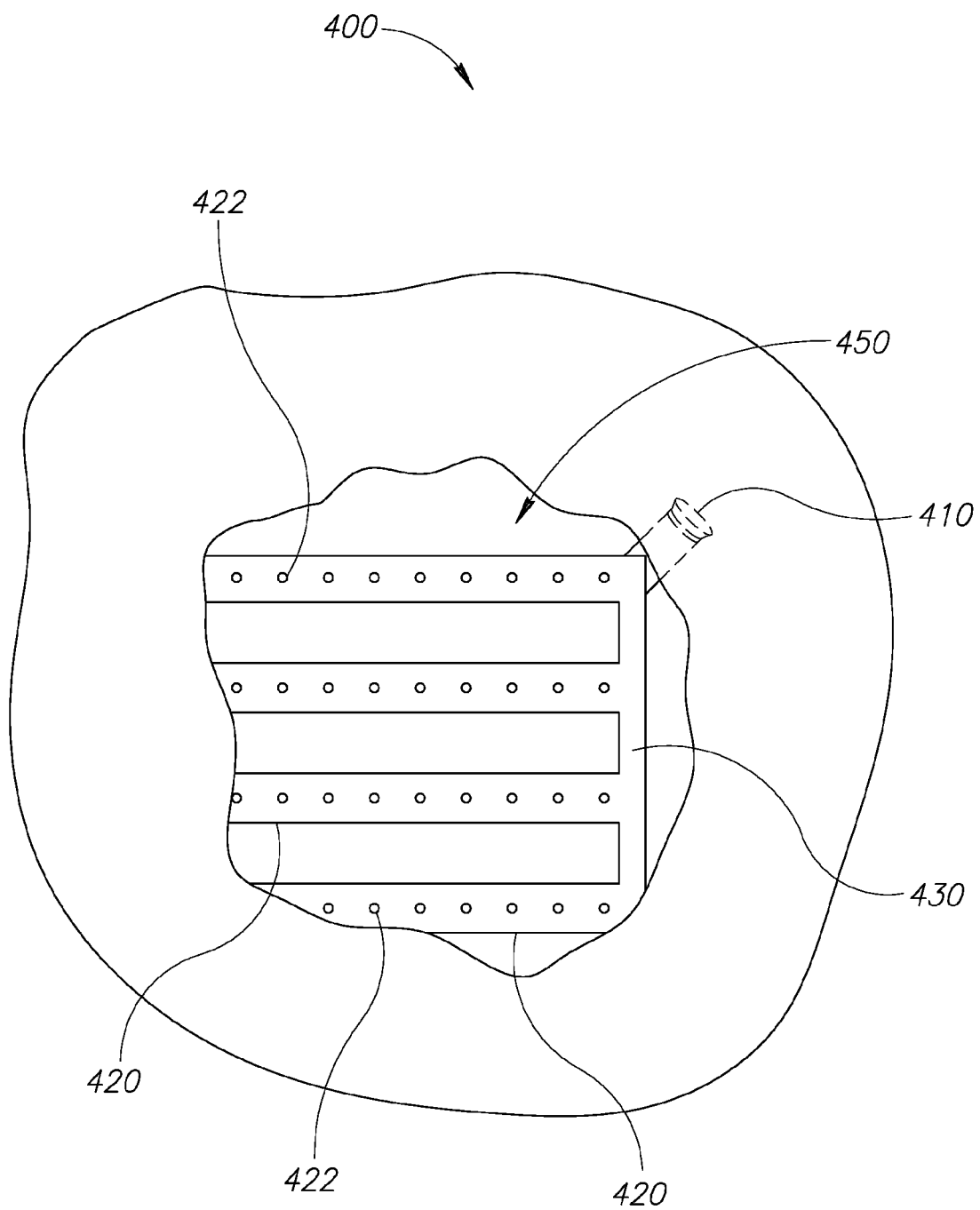
FIG. 4, schematically illustrates a scalp cover including an internal sprinkler channel structure according to some embodiments.

Reference is now made to FIG. 4, which schematically illustrates a bottom view of a scalp cover 400, optionally similar to that disclosed in FIG. 2 or FIG. 3 having an inner sprinkler channel structure 450. Inner sprinkler channel structure 450 includes a plurality of sprinkler channels 420, each channel having a plurality of apertures/pores 422, through which the supplied gas (and optionally also the aqueous liquid) may be essentially evenly distributed to and/or around the subject's scalp and/or hair (not shown). Sprinkler channel structure 450 is here shown to include 4 sprinkler channels; however, a different number of channels (e.g. 2, 5 or 10 channels) is also applicable and thus within the scope of this disclosure. Similarly, sprinkler channels 420 are here shown to be positioned in rows. However, other configurations are also possible and thus within the scope of this disclosure. Likewise, sprinkler channels 420 are here shown to include 7-9 essentially evenly distributed apertures/pores. However, different number of pores as well as an uneven distribution thereof (e.g. different longitudinal and/or axial spacing) is also applicable, and thus within the scope of this disclosure. Optionally, sprinkler channel structure 450 may also include a connecting channel 430 configured to interconnect sprinkler channels 420 of sprinkler channel structure 450, such that the gas (and/or aqueous liquid) supplied through inlet 410 will be distributed to all of sprinkler channels 420 and from there through apertures/pores 422 to the subject's scalp and/or hair.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. According to some embodiments, the term "comprising" may be replaced by the term "consisting essentially of" or "consisting of".

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and subcombinations thereof. It is therefore intended that the following appended claims and claims hereafter introduced be interpreted to include all such modifications, additions and sub-combinations as are within their true spirit and scope.

The invention claimed is:

1. A method for shave-free trans-cranial focused ultrasound (FUS) treatment, the method comprising;
   placing a scalp cover on a head of a subject in need of trans-cranial FUS, such that said scalp cover seals around the subject's scalp;
   supplying a gas into the scalp cover such that ambient air covering the subject's scalp is replaced by the supplied gas; wherein the gas has a higher solubility in water than the ambient air;
   sending a flow of an aqueous fluid into the scalp cover such that the subject's hair is submerged and/or wet; and
   providing a trans-cranial focused ultrasound (FUS) treatment to the subject.

2. The method of claim 1, wherein the trans-cranial focused ultrasound (FUS) treatment comprises high-intensity focused ultrasound (HIFU), low-intensity focused ultrasound (LIFU), FUS-induced BBB opening or FUS-mediated neuromodulation.

3. The method of 1, further comprising administering a contrast agent prior to the treatment.

4. The method of 1, further comprising administering a drug during or after the treatment.

5. The method of 1, wherein the gas has a solubility in water above 1 g/L at 25° C. at 100 kPA.

6. The method of claim 1, wherein the gas is $CO_2$.

7. The method of 1, wherein the aqueous fluid is degassed water or a hydrogel.

8. The method of 1, wherein the providing of the trans-cranial FUS treatment to the subject comprises placing a helmet like head wearable, housing a FUS transducer, on top of the scalp cover.

9. The method of claim 1, wherein the scalp cover is made of a material transparent to the FUS.

10. The method of claim 1, wherein the supplying of the gas into the scalp cover comprises sending the flow of the gas through an inlet formed in the scalp cover.

11. The method of claim 1, wherein the flowing of the aqueous fluid into the scalp cover comprises sending the flow of the aqueous fluid through the same or a different outlet formed in the scalp cover.

12. The method of claim 1, wherein replacing the ambient air comprises allowing ambient air to exit said scalp cover through an outlet formed therein.

13. The method of claim 1, wherein the FUS treatment is provided without prior shaving of the subject's hair.

14. A device configured to facilitate shave-free trans-cranial focused
   ultrasound (FUS) treatment, the device comprising a scalp cover, the scalp cover comprising:
   a first inlet configured to allow supply of a gas into said scalp cover, and
   an outlet configured to allow outflow of ambient air contained within said scalp cover when said gas is being supplied, such that the ambient air contained within the scalp cover is replaced by the supplied gas,
   wherein the supplied gas has a higher solubility in water than the ambient air,
   wherein said outlet is configured to be closed when the ambient air has been replaced by said supplied gas,
   wherein said first inlet is positioned on an opposite side of said scalp cover than said outlet,
   wherein said first inlet or a second inlet are configured to allow supply of an aqueous fluid into said scalp cover such that a subject's hair is submerged and/or wet, and
   wherein said scalp cover is sized and shaped to seal said scalp cover around a the subject's scalp, when worn.

15. The device of claim 14, wherein the scalp cover is made from a material configured to allow undisturbed passage of the FUS therethrough.

16. The device of claim 14, wherein said first and/or said second inlet comprises a valve wherein the valve is a one-way valve configured to prevent backflow of said supplied gas and/or said aqueous fluid.

17. A device configured to facilitate shave-free trans-cranial focused ultrasound (FUS) treatment, the device comprising a scalp cover, the scalp cover comprising:
   a first inlet configured to allow supply of a gas into said scalp cover,
   an outlet configured to allow outflow of ambient air contained within said scalp cover when said gas is being supplied, such that the ambient air contained within the scalp cover is replaced by the supplied gas, and wherein the supplied gas has a higher solubility in water than the ambient air,
   a sensor configured to determine the concentration of the gas within said scalp cover, wherein said first inlet or a second inlet are configured to allow supply of an aqueous fluid into said scalp cover such that a subject's hair is submerged and/or wet, and wherein said scalp cover is sized and shaped to essentially seal said scalp cover around the subject's scalp, when worn.

\* \* \* \* \*